United States Patent [19]

Su et al.

[11] 4,329,334
[45] May 11, 1982

[54] ANIONIC-AMPHOTERIC BASED ANTIMICROBIAL SHAMPOO

[75] Inventors: Dean T. Su, North Brunswick; Warren R. Schubert, Somerset, both of N.J.

[73] Assignee: Colgate-Palmolive Company, New York, N.Y.

[21] Appl. No.: 205,802

[22] Filed: Nov. 10, 1980

[51] Int. Cl.³ .......................... A61K 7/06; A61K 7/09; A61K 31/415
[52] U.S. Cl. ........................................ 424/70; 424/71; 424/273 R; 424/DIG. 4; 252/106; 252/DIG. 13
[58] Field of Search ......... 424/70, 71, 273 R, DIG. 4; 252/DIG. 13, 106

[56] References Cited

U.S. PATENT DOCUMENTS

| | | | |
|---|---|---|---|
| 3,658,985 | 4/1972 | Olson, Jr. et al. | 424/70 |
| 3,812,142 | 5/1974 | Meiser et al. | 424/269 |
| 3,903,287 | 9/1975 | Meiser et al. | 424/273 |
| 3,950,417 | 4/1976 | Verdicchio et al. | 424/70 |
| 3,996,146 | 12/1976 | Tarasov et al. | 424/70 |
| 4,154,706 | 5/1979 | Kenkare et al. | 252/DIG. 13 |

FOREIGN PATENT DOCUMENTS 1502144  2/1978  United Kingdom .

Primary Examiner—Donald B. Moyer
Attorney, Agent, or Firm—Richard N. Miller; Murray M. Grill; Herbert S. Sylvester

[57] ABSTRACT

A homogeneous liquid anionic-amphoteric based antimicrobial conditioning shampoo which includes about 0.5 to 2.5% of the antimicrobial agent, 1-imidazolyl-1-(4-chlorophenoxy)-3,3-dimethylbutan-2-one, solubilized in an aqueous solution of critical amounts of a mixture of the following specific ingredients:

a. about 10–40% by weight of an anionic sulfate or sulfonate surface active agent,
b. about 0.1–7.5% by weight of an amphoteric surfactant selected from the group consisting of cocobetaine, cocosulfobetaine, cocoamidopropylbetaine, cocoamidopropylsulfobetaine or combinations thereof.
c. about 1–6% by weight of a fatty acid mono- or di-ethanolamide, and preferably
d. about 1.1–5% by weight of a nonionic surface active agent selected from the group consisting of a tertiary amine oxide, a polyoxyethylene hexitan mono-higher fatty acid ester, and mixtures thereof, and
e. about 0.5–2% by weight of a lower aliphatic monohydric or polyhydric alcohol or mixtures thereof.

9 Claims, No Drawings

ANIONIC-AMPHOTERIC BASED ANTIMICROBIAL SHAMPOO

This invention relates to an anionic-amphoteric based antimicrobial shampoo containing the water-insoluble antimicrobial agent, 1-imidazolyl-1-(4-chlorophenoxy)-3,3-dimethylbutan-2-one, solubilized in an aqueous solution of critical amounts of specific amphoteric and anionic components, capable of both cleansing and conditioning the hair in a single operation, by simply washing the hair therewith.

PRIOR ART

The prior art antidandruff shampoos contain organo-zinc compounds such as zinc pyrithione, which is not soluble in a liquid shampoo, resulting in a potentially non-homogeneous, milky shampoo wherein the insoluble antidandruff agent is unevenly dispersed in and/or precipitates out of the shampoo composition.

The imidazolyl ketones such as 1-imidazolyl-1-(4 chlorophenoxy)-3,3-dimethylbutan-2-one, are disclosed in U.S. Pat. Nos. 3,812,142 and 3,903,287 as antimycotic agents, useful in pharmaceutical compositions including aqueous suspensions containing surface active agents such as polyoxyethylene sorbitan fatty acid esters. British Pat. No. 1,502,144 and its German counterpart, Patent No. 2,430,039, disclose cosmetic compositions such as shampoos containing the imidazolyl ketone antimycotic agents dispersed in a dermatologically acceptable carrier which contains a detergent-active compound. The shampoos are in the form of creams, aerosols, powders and liquids. Although nonionic, amphoteric and cationic surfactants are listed, the specific liquid shampoos disclosed contain 50% anionic surfactant and 3.5–5% of the nonionic fatty acid diethanolamide in 44–45.5% water. German Pat. No. 2,600,800 discloses the 1-imidazolyl-1-(4-chlorophenoxy)-3,3-dimethylbutan-2-one in a fungicidal composition, which may be in the form of a dispersion in water, as useful for protecting plaster coatings, dispersion dyes, wall-paper, tiled surfaces, paints, glues, bitumina, furniture, leather, shower curtains, textiles, carpets, wood and paper. German Pat. No. 2,700,806 also discloses a mixture of the imidazolyl ketone fungicide and a quaternary ammonium bactericide useful for protecting materials such as paints, glues, bitumen, cellulose, paper, textiles, leather and wood.

Although the prior art discloses the specified imidazolyl ketone as an antimycotic agent, and its use in various formulations including shampoos, said liquid compositions are usually in the form of suspensions and/or dispersions. When in suspension form, this is due to the water-insolubility property of the imidazolyl ketones which results in opaque and milky non-homogeneous liquid shampoos, similarly to the organozinc-containing shampoos.

In addition to an antidandruff agent, shampoos must include surfactants, usually based on anionic detergents, as shown in aforedescribed British Pat. No. 1,502,144. However, nonionic and amphoteric detergents may be present in addition to said anionic detergents as shown by U.S. Pat. No. 3,950,417, wherein the aqueous shampoo composition comprises an amphoteric agent such as the betaines, an anionic surfactant and a water soluble nonionic surfactant such as polyoxyethylene (20) sorbitan monolaurate in the weight ratio of 1:1:3 respectively. Similarly, U.S. Pat. No. 3,658,985 discloses an oil and fluorescent dye containing liquid shampoo comprising a detergent mixture of 10–35% anionic sulfate or sulfonate type detergent, up to 10% alkalolamides, and 0–10% lower aliphatic alcohol or a mixture of amphoteric and cationic surfactants, in lieu of the anionic detergent. U.S. Pat. No. 3,849,548 also discloses a multidetergent liquid shampoo containing amphoteric betaine, anionic sulfonate or sulfate in an aqueous or aqueous alcoholic vehicle, and containing an aminopolyurea resin as an antimicrobial agent. A betaine and anionic surfactant containing liquid shampoo is also disclosed in U.S. Pat. No. 4,148,762. U.S. Pat. No. 4,013,787 further discloses a film forming cationic polymer conditioning agent in cosmetic hair compositions including nonionic based as well as amphoteric-anionic based liquid shampoos. U.S. Pat. No. 3,996,146 further discloses an acid pH clear shampoo comprising 0.05–2.5% of a quaternary ammonium polymer conditioning agent in a multidetergent system containing 10–25% of at least two anionic detergents and 4–15% of an amphoteric surfactant such as betaine.

However, there is no disclosure of the imidazolyl ketone antimicrobial agent solubilized in the instant specified anionic-amphoteric based aqueous conditioning shampoo containing an ethanolamide and preferably a nonionic polyoxyethylene higher fatty acid ester and/or a tertiary amine oxide, and a lower aliphatic monohydric or polyhydric alcohol.

DESCRIPTION OF THE INVENTION

It has now been found that a mixture of specified anionic and amphoteric components in critical amounts solubilizes the insoluble imidazolyl ketone in an aqueous solution and retains said ketone in solution, in the production of a homogeneous liquid antimicrobial conditioning shampoo.

Accordingly, it is an object of present invention to provide a homogeneous liquid antimicrobial shampoo.

Another object of this invention is to provide a liquid shampoo capable of both cleansing and conditioning the hair in a single operation.

Still another object of this invention is to provide an aqueous liquid antimicrobial shampoo containing 1-imidazolyl-1-(4-chlorophenoxy)-3,3-dimethylbutan-2-one solubilized in said aqueous medium.

Another object of this invention is to provide an anionic and amphoteric based shampoo capable of solubilizing aforesaid imidazolyl ketone antimicrobial agent in the production of a clear homogeneous liquid shampoo.

Other objects of this invention will become apparant to those skilled in the art upon reading the following specification.

Accordingly, the present invention relates to a homogeneous liquid anionic-amphoteric based antimicrobial conditioning shampoo containing an effective antimicrobial amount of 1-imidazolyl-1-(4-chlorophenoxy)-3,3-dimethylbutan-2-one solubilized in an aqueous vehicle containing an anionic sulfate or sulfonate surfactant; an amphoteric surfactant selected from the group consisting of betaines, sulfobetaines, amidobetaines, amidosulfobetaines and mixtures thereof; a fatty acid mono- or di-ethanolamide; and preferably a nonionic tertiary amine oxide and/or a polyoxyethylene hexitan monohigher fatty acid ester; and a lower aliphatic mono- or polyhydric alcohol as the essential components in certain specified amounts.

The antimicrobial agent utilized in instant invention is 1-imidazolyl-1-(4-chlorophenoxy)-3,3-dimethylbutan-2-one having the structural formula:

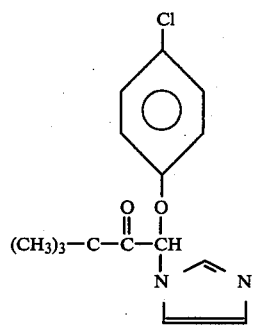

which is prepared by reacting 1-bromo-1-(4-chlorophenoxy)-3,3-dimethylbutan-2-one with imidazole dissolved in acetonitrile as disclosed in U.S. Pat. Nos. 3,812,142 and 3,903,287 which are made a part of this specification. This imidazolyl ketone is a water insoluble crystalline powder having a melting point of 94.5°–97.8° C. which may be obtained from the Bayer Company.

Solubility studies using 2 g. of the imidazolyl antimicrobial agent plus 5 g. polyoxyethylene (20) sorbitan monolaurate (Tween 20) or 5 g. lauric myristic diethanolamide (LMDEA) or mixtures of 4, 3, 2, 1 g. Tween 20 and 1, 2, 3, 4 g. LMDEA respectively in 93 g. of water, showed that the resultant liquid was cloudy and the ingredients separated out. Similarly, poor solubility results were obtained by combining 3.5 g. of a solution of 100 g. imidazolyl ketone agent in 250 g. LMDEA with 16.7 g. myristyl dimethylamine oxide (30% active) (MO) in 79.8 g. water, or with 8.4 g. MO in 88.1 g. water, or with 3.3 g MO in 9.2 g. water, wherein the resultant products were cloudy with fine precipitates. On the other hand, when 3.5 g. of the aforedefined imidazolyl solution in LMDEA was mixed with 33.3 g. MO in 63.2 g. water, a clear solution was obtained. This 33.3 g. MO represents a 10% active content, whereas the cloudy products represent 5%, 2.5% and 1% active concentrations respectively.

Clear, watery solutions were also obtained when 3.5 g. of the aforedefined imidazolyl solution in LMDEA was mixed with 61.1 g. triethanolammonium lauryl sulfate (TEALS) solution (41% active concentration) in 35.4 g. water; with 48.5 g. TEALS solution in 48 g. water; with 24.4 g. TEALS solution in 72.1 g. water; and with 12.2 g. TEALS solution in 84.3 g. water; a 25%, 20%, 10%, and 5% TEALS amount respectively. The addition of 25%, 20%, 10% and 5% respectively of an aqueous solution (28% active) of a sodium sulfate salt of a $C_{12}$–$C_{14}$ alcohol condensed with 3 moles of ethylene oxide (Standapol ES-3) to 3.5 g. of the aforesaid imidazolyl-LMDEA solution also resulted in clear, watery solutions.

Thus, it is apparent that the amounts and specificity of ingredients are critical in order to solubilize the antimicrobial agent in an aqueous medium in order to obtain a clear shampoo. It has further been found that the imidazolyl compound must first be solubilized in a nonionic medium prior to the addition of ionic materials thereto.

It has additionally been found that this antimicrobial agent is nonionic as a result of steric hindrance effects. The effective concentration of the antimicrobial agent useful in present aqueous shampoo vehicle is preferably about 0.5–2.5% by weight of the total shampoo.

Accordingly, the shampoo vehicle constitutes about 65–80% water containing critical amounts of specifically essential anionic and amphoteric compounds to effect an aqueous vehicle for dissolution of aforesaid antimicrobial agent.

The essential anionic and amphoteric components contained in this shampoo comprise an anionic sulfate or sulfonate surfactant, an amphoteric surfactant such as the betaine or sulfobetaine or amidobetaine or amidosulfobetaine, a higher fatty acid ethanolamide and preferably a nonionic surfactant selected from the group consisting of a tertiary amine oxide and/or a polyethoxylated hexitan fatty acid ester and a lower aliphatic mono- and/or polyhydric alcohol in certain critical amounts in order to avoid precipitation of the antimicrobial agent.

More specifically, the instant antimicrobial shampoo is based on the essential components comprising about 10–40% and preferably 12–25% by weight of an anionic sulfate or sulfonate surfactant, about 0.1–7.5% and preferably 0.5–5% by weight of an amphoteric agent selected from the group consisting of betaine, sulfobetaine, alkyl amidobetaine, alkyl amidosulfobetaine and mixtures thereof, about 1–6% by weight of a higher fatty acid mono- or di-ethanolamide, and preferably about 1–5% by weight of a nonionic surfactant selected from the group consisting of a polyoxyethylene hexitan mono-higher fatty acid ester having about 20 moles of ethylene oxide per mole, and a dimethyl higher alkyl tertiary amine oxide and mixtures thereof, and about 0.5–2% by weight of a lower aliphatic monohydric and/or polyhydric alcohol.

The anionic sulfate or sulfonate surface active agent provides strong cleansing action to the composition. Examples of suitable anionic detergents which fall within the scope of this anionic detergent class include the water-soluble salts, e.g., the sodium, ammonium, and alkylolammonium salts, of the water-soluble sulfated and sulfonated synthetic detergents having an alkyl radical or 10–18 carbon atoms in their molecular structure. (The term alkyl includes the alkyl portion of the higher acyl radicals.)

A preferred group of anionic surfactants may be represented by the following general formula:

$$R_1-O(CH_2CH_2O)_nSO_3M$$

wherein $R_1$ is an alkyl radical having 10–18 carbon atoms, n is an integer having the value of 0–5 and M is an alkali metal, ammonium, alkylolammonium or an organic amine. Other suitable anionic detergents are the long-chain hydroxyalkane sulfonates and paraffin sulfonates containing 10–18 carbon atoms; sodium and potassium sulfates of higher alcohols containing 8–18 carbon atoms such as sodium lauryl sulfate and sodium tallow alcohol sulfate; sodium and potassium salts of α-sulfofatty acid esters containing about 10–18 carbon atoms in the acyl group, e.g., methyl α-sulfotallowate, ammonium sulfates of mono- or diglycerides of higher ($C_{10}$–$C_{18}$) fatty acids, e.g., stearic monoglyceride monosulfate; sodium higher alkyl ($C_{10}$–$C_{18}$) glyceryl ether sulfonates; and sodium or potassium alkyl phenol polyethenoxy ether sulfates with about 1–6 oxyethylene groups per molecule and in which the alkyl radicals contain about 8 to about 18 carbon atoms.

The suitable anionic detergents include also the $C_8$-$C_{18}$ acyl sarcosinates (e.g., sodium lauroyl sarcosinate), sodium and potassium salts of the reaction product of higher fatty acids containing 8-18 carbon atoms in the molecule esterified with isethionic acid, and sodium and potassium salts of the $C_8$-$C_{18}$ acyl N-methyl taurides, e.g., sodium cocoyl methyl taurate and potassium stearoyl methyl taurate.

The particular anionic detergent salt will be suitably selected depending upon the particular formulation and the proportions therein. Suitable salts include the ammonium, substituted ammonium (mono-, di- and triethanolammonium), and alkali metal (such as sodium and potassium) salts. Preferred salts are the ammonium, triethanolammonium, sodium and potassium salts of the higher alkyl sulfates and the $C_8$-$C_{18}$ acyl sarcosinates.

The amphoteric surfactant component of instant liquid shampoo formulation provides increased viscosity, mild cleansing and strong conditioning action to the composition, and is selected from the group consisting of betaines, sulfobetaines, amidobetaines, amidosulfobetaines and mixtures thereof, having the following general formula:

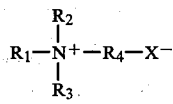

wherein $R_1$ is an alkyl group having 10 to about 20 carbon atoms, preferably 12 to 16 carbon atoms or the amido radical:

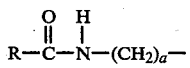

wherein R is an alkyl group having about 10 to 20 carbon atoms and a is the integer 1 to 4; $R_2$ and $R_3$ are each alkyl groups having 1 to 3 carbons and preferably 1 carbon; $R_4$ is an alkylene or hydroxyalkylene group having from 1 to 4 carbon atoms and, optionally, one hydroxyl group; and X is an anion selected from the group consisting of $SO_3=$ and $COO=$. Typical alkyldimethyl betaines include decyl dimethyl betaine or 2-(N-decyl-N,N-dimethylammonio) acetate, coco dimethyl betaine or 2-(N-coco-N,N-dimethyl-ammonio) acetate, myristyl dimethyl betaine, palmityl dimethyl betaine, lauryl dimethyl betaine, cetyl dimethyl betaine, stearyl dimethyl betaine, etc. Typical sulfobetaines or sultaines similarly include coco dimethyl sulfobetaine, or 3-(N-coco-N,N-dimethyl ammonio) propane-1 sulfonate, myristyl dimethyl sulfobetaine, palmityl dimethyl sulfobetaine, lauryl dimethyl sulfobetaine, etc. The amidobetaines and amidosulfobetaines similarly include cocoamidoethyl betaine, cocoamidoethylsulfobetaine, and the like.

The polyoxyethylene hexitan mono-higher fatty acid ester nonionic component which is preferably an additional ingredient of present liquid shampoo provides cleaning action and functions as a dispersant. The useful compounds in this group include esters having from 10-20 carbon atoms in the higher fatty acyl thereof and 4-100, preferably 10-80, moles of ethylene oxide per mol. Preferably, the hexitan is sorbitan, although mannitan and other hexitans are also often useful, the higher fatty acyl will be of 10-16 or 20 carbon atoms, more preferably of 12-16 or 18 carbon atoms and most preferably of about 12 carbon atoms, and the number of ethoxies will be from 15-80, often preferably about 20. Especially useful is an I.C.I. America, Inc. product sold under the trade name Tween 20, also known as polysorbate 20 which is polyoxyethylene (20) sorbitan monolaurate. Similarly useful products are sold under similar identifications, such as Tween 40, 60, 65 and 80, all of which are nonionic surface active agents wherein the higher fatty acyl is, palmitoyl, stearoyl or oleyoyl and the number of mols of ethylene oxide per mol is about 20. However, of these materials the polyoxyethylene (20) sorbitan monolaurate is usually favored.

The amine oxide nonionic component which is a preferably additional ingredient of instant liquid shampoo provides both cleaning and conditioning properties to the shampoo, and is nonionic in the pH range of the shampoo, which is normally within the range of 6.5 to 7.5 and preferably 6.8 to 7.3 or about 7. The amine oxides useful herein have the structural formula:

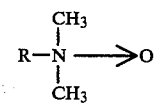

wherein R is an alkyl radical of 10-16 carbons. Examples of suitable amine oxides include dimethyl laurylamine oxide, dimethyl cetylamine oxide and dimethyl myristylamine oxide. Of course, as with the other components of the present composition, the amine oxides will usually be chosen for desired solubility in the aqueous medium employed and for compatibility with the other components of the shampoo.

The ethanolamide component of instant liquid shampoo functions primarily as a foam booster. Useful compounds in this group include mono- and di-ethanolamides of higher fatty acids having about 8-18 carbon atoms. Specific examples of suitable ethanolamides include cocomonoethanolamide, cocodiethanolamide, lauric myristic diethanolamide, lauric monoethanolamide, or combinations thereof.

The lower aliphatic alcohol component, which is an optional but a preferably additional ingredient in the instant clear liquid shampoo, enhances the cleansing action of the shampoo and promotes the solubility of the imidazolyl antimicrobial agent in the multidetergent aqueous vehicle. The alcohol useful herein may be a lower aliphatic monohydric or polyhydric alcohol containing 2 to 3 carbon atoms, such as ethyl, propyl and isopropyl alcohol, propylene glycol and glycerine or mixtures thereof.

All of the aforesaid components in this shampoo are water-soluble and remain water-soluble during storage of the shampoo.

The particular combination of anionic sulfate or sulfonate, amphoteric betaine, and ethanolamide with or without the nonionic surfactant and/or alcohol provides a balanced, anionic and amphoteric surface active system which solubilizes the antidandruff agent and has desirable foaming, lathering, detersive and conditioning properties, as well as desirable viscosity characteristics. The resultant homogeneous liquid shampoo is capable of both washing and conditioning the hair in a single operation by simply shampooing. An additional and essential function of the instant anionic-amphoteric based shampoo is the concommitant antimicrobial action afforded by the specific imidazolyl ketone.

In addition to the previously mentioned constituents of the liquid shampoo one may also employ normal and conventional adjuvants, provided they do not adversely affect the properties of the shampoo. Thus, there may be used various coloring agents and perfumes; ultraviolet light absorbers such as the Uvinuls, which are products of GAF Corporation; preservatives such as formaldehyde or hydrogen peroxide; pearlescing agents and opacifiers; lubricants, such as mineral oil and higher fatty alcohols, e.g., cetyl alcohol, stearyl alcohol; quaternary antibacterial materials such as Arquad B-100 (Dimethylalkylbenzylammonium chloride); viscosity modifiers such as polyethylene glycol distearate of a molecular weight in the range of 2000–8000; sequestering agents such as EDTA tetrasodium salt, sodium chloride, etc. The proportion of such adjuvant materials, in total, will normally not exceed 5% of the shampoo, and preferably less than 2% thereof. The percentages of most of such individual components will be less than 2% and preferably less than 1%.

The present shampoos are readily made by simple mixing methods from readily available components which, on storage, do not adversely affect the entire composition. However, it is essential that the imidazolyl compound be first mixed with the nonionic components such as the ethanolamide, the polysorbate and the alcohol, if present, prior to the addition of the amphoteric and anionic surfactants. Thus, the products are capable of being made in desired clear form or in opaque or opalescent form. The viscosities are adjustable by changing the total percentage of active ingredients and by modifying the percentages of thickening agent, sodium chloride and other adjuvants. In all such cases the product made will be pourable from a relatively narrow mouth bottle (1.5 cm. diameter) and the shampoo will not be so thin as to run off the hair or hands. The viscosity of the shampoo will normally be about that of glycerin at room temperature, e.g., about 1,000 centipoises, but the viscosity may be in the broader ranges of 250–2,000 and 50–5,000 centipoises. Its viscosity may approximate those of commercially acceptable shampooes now on the market. Instead of measuring viscosity directly, as by a Brookfield LVF viscosimeter, one may employ standard laboratory flow tests, in which flow times through a restriction or tube length under a reproducible head are measured in seconds, utilizing a Raymond tube. Viscosities may preferably range from 10–135 seconds and up to 300 or 400 seconds. The shampoo viscosity and the shampoo itself remain stable on storage for lengthy periods of time, without color changes or settling out of any insoluble materials.

These products have unexpectedly desirable properties. For example, the foam quality and lubricity is comparable to standard shampoos based on triethanolamine lauryl sulfate. Further, such shampoos clean the hair exceptionally well and leave it easy to comb, manageable and of low raspiness, are less drying, leaving the hair with a softer feel, producing fewer split ends after shampooing, and being easier to comb and causing less flyaway effect.

The following examples illustrate but do not limit the invention. Unless otherwise mentioned, all percentages in the examples and elsewhere in the specification are by weight and all temperatures are in °C.

Clear Antidandruff Shampoos

EXAMPLE 1

|  | % |
|---|---|
| LONZAINE CS (coco amidopropyl sulfobetaine)* | 2.5 |
| TEALS (triethanolammonium lauryl sulfate) | 15.0 |
| LMDEA (lauric myristic diethanolamide) | 5.0 |
| Polysorbate 20 (polyoxethylene (20) sorbitan monolaurate) | 2.0 |
| Climbazole (Bayer Co.) (1-imidazolyl-1-(4-chlorophenoxy)-3,3-dimethylbutan-2-one) | 2.0 |
| Formaldehyde | 0.2 |
| Propylene glycol | 1.0 |
| Water | 72.3 |

*N-cocoamidopropyl-N,N-dimethyl-N-2 hydroxy propyl-1-sulfonate.

The Climbazole, LMDEA, propylene glycol and the Polysorbate 20 are mixed together until homogeneous and clear. 7.1% by weight of a 35% aqueous solution of Lonzaine CS is subsequently added with agitation, followed by the addition of TEALS. Water and formaldehyde are added lastly with agitation. This product is a clear solution with no sign of particulate suspension or precipitation. It is very important to first dissolve the Climbazole in the LMDEA propylene glycol and Polysorbate 20 to give a clear and viscous solution.

The resultant product is an excellent conditioning shampoo of desired viscosity, foaming power, foam stability, antimicrobial activity and good shampooing effects, i.e., leaves the wet hair easy to comb, with a soft feel and static free.

In the shampooing described herein and in subsequent examples the human hair is washed on the head by wetting the hair with warm tap water at about 42° C., applying 15 grams of shampoo to the hair, lathering it into the hair for a minute, rinsing with warm tap water for 30 seconds, re-lathering with 7 grams of shampoo for a minute and rinsing off for 30 seconds, after which the hair is towel dried and dried further with an automatic hair dryer.

EXAMPLE 2

|  | % |
|---|---|
| TEALS | 17.0 |
| LONZAINE CS | 2.4 |
| Ammonyx MO (dimethyl myristylamine oxide) | 2.0 |
| Lemon oil | 2.0 |
| Climbazole | 1.5 |
| LMDEA | 1.5 |
| Formaldehyde | 0.1 |
| Deionized water (D. I. water) | 73.5 |

The Climbazole, LMDEA and the lemon oil are mixed well until no particulate material is evident. 6.8% by weight of a 35% aqueous Lonzaine CS solution is added with stirring, followed by the addition of 6.7% by weight of a 30% aqueous Ammonyx MO solution while continuously mixing. 41.5% by weight of a 40.9% aqueous TEALS solution is added followed by the water and formaldehyde with stirring. This product is a clear solution.

EXAMPLE 3

|  | % |
|---|---|
| TEALS | 16.5 |
| LMDEA | 2.5 |

|  | % |
|---|---|
| Lonzaine CS | 2.1 |
| Ammonyx MO | 2.1 |
| Climbazole | 2.0 |
| Formaldehyde | 0.1 |
| D. I. water | 74.7 |

This product is prepared in accordance with the procedure of Example 2, except that the lemon oil is omitted.

EXAMPLE 4

|  | % |
|---|---|
| TEALS | 17.0 |
| Lonzaine C (cocoamidopropyl betaine)* | 4.8 |
| Ammonyx MO | 4.0 |
| LMDEA | 2.0 |
| Climbazole | 2.0 |
| Formaldehyde | 0.1 |
| D. I. water | 70.1 |

*N-cocoamidopropyl-N,N-dimethyl ammonio acetate.

This shampoo, prepared in accordance with the process of Example 3, is clear and has a viscosity of 48.6 seconds (Raymond tube).

EXAMPLE 5

Example 4 is repeated but the Ammonyx MO content is reduced to 3% and the water content is adjusted accordingly.

The viscosity of the resulting clear liquid shampoo is reduced to 47.5 seconds.

EXAMPLE 6

Example 4 is repeated but the Ammonyx MO content is reduced to 2% and the water content is adjusted accordingly.

The viscosity of the resulting clear liquid shampoo is reduced to 44.9 seconds.

The products of Examples 2–6 possess similarly good antimicrobial, cleansing and conditioning properties.

EXAMPLE 7

|  | % |
|---|---|
| TEALS | 16.0 |
| LMDEA | 5.0 |
| Polysorbate 20 | 3.0 |
| Climbazole | 2.0 |
| Sodium chloride (NaCl) | 1.0 |
| Lemon oil | 0.5 |
| Lonzaine CS | 0.5 |
| D. I. water | 72.0 |

The resultant shampoo is clear and has a viscosity of 35.4 seconds (Raymond tube).

EXAMPLE 8

|  | % |
|---|---|
| TEALS | 16.0 |
| LMDEA | 5.0 |
| Polysorbate 20 | 3.0 |
| Climbazole | 2.0 |
| NaCl | 1.0 |
| Lonzaine CS | 1.0 |
| D. I. water | 72.0 |

This shampoo is a clear liquid and has a viscosity of 38 seconds (Raymond tube).

EXAMPLE 9

|  | % |
|---|---|
| TEALS | 16.0 |
| LMDEA | 5.0 |
| Polysorbate 20 | 3.0 |
| Climbazole | 2.0 |
| NaCl | 1.0 |
| Lonzaine CS | 1.5 |
| D. I. water | 71.5 |

This shampoo is a clear liquid and has a viscosity of 38.5 seconds (Raymond tube).

Increasing the Lonzaine CS content from 0.5 to 1.5% increases the viscosity of the liquid shampoo.

EXAMPLE 10

|  | % |
|---|---|
| TEALS | 15.0 |
| Lonzaine C (cocoamidopropyl betaine)* | 4.5 |
| LMDEA | 4.0 |
| Climbazole | 2.0 |
| Fragrance | 1.0 |
| D. I. water | 73.5 |

*N-cocoamidopropyl-N,N-dimethyl ammino acetate.

This product is a clear liquid with a viscosity of 25.2 seconds.

EXAMPLE 11

|  | % |
|---|---|
| TEALS | 15.5 |
| Lonzaine CS | 3.0 |
| LMDEA | 4.5 |
| Polysorbate 20 | 1.5 |
| Climbazole | 2.0 |
| NaCl | 1.0 |
| Fragrance | 1.0 |
| D & C Orange No. 4 (1%) | 0.025 |
| D & C Green No. 3 (1%) | 0.025 |
| D. I. water | 71.45 |

This shampoo is a clear tinted liquid having a viscosity of 47 seconds.

EXAMPLE 12

|  | % |
|---|---|
| Standapol ES-3 (sodium lauryl EO 3:1 sulfate) | 20.0 |
| Ammonyx MO | 2.1 |
| Ethyl alcohol | 2.0 |
| Polysorbate 20 | 2.0 |
| LMDEA | 1.0 |
| Propylene glycol | 1.0 |
| Climbazole | 2.0 |
| NaCl | 1.0 |
| EDTA Tetrasodium salt (tetrasodium ethylene diamine tetra-acetate) | 0.1 |
| Fragrance | 1.0 |
| Citric acid | 0.25 |
| FD & C Blue No. 1 (0.1%) | 0.1 |

-continued

| | % |
|---|---|
| D & C Red No. 19 (0.1%) | 0.4 |
| D. I. water | 67.05 |

This shampoo is a clear tinted liquid with a viscosity of 108.7 seconds.

EXAMPLE 13

| | % |
|---|---|
| TEALS | 16.0 |
| LMDEA | 4.0 |
| Lonzaine CS | 2.5 |
| Propylene glycol | 1.0 |
| Polysorbate 20 | 1.0 |
| NaCl | 1.5 |
| Climbazole | 2.0 |
| Fragrance | 1.0 |
| D. I. water | 71.0 |

This clear liquid shampoo has a viscosity of 41 seconds.

EXAMPLE 14

Example 13 is repeated except that 16.5% Standapol ES-3 is substituted for 16% TEALS, and the water content is adjusted accordingly. The resultant clear shampoo product has a low viscosity.

EXAMPLE 15

Example 13 is repeated except that the TEALS content is increased to 17.5% and the NaCl is omitted. The resultant shampoo is a clear liquid with a viscosity of 75.6 seconds.

The fragrance may be omitted if desired.

The Climbazole can be increased to 5% and still yield a clear solution.

EXAMPLE 16

Example 15 is repeated except that 1% ethyl alcohol and 0.125% D & C Green No. 5 coloring are added, the Polysorbate 20 is omitted, and the water content is adjusted accordingly. The resulting clear green liquid shampoo has a viscosity of 124 seconds.

EXAMPLE 17

Example 15 is repeated except that the propylene glycol is omitted and 0.125% D & C Green No. 5 coloring is added, and the water content adjusted accordingly. The resultant product is a clear green liquid with a viscosity of 118 seconds.

EXAMPLE 18

Example 15 is repeated except that 1% ethyl alcohol and 0.125% D & C Green No. 5 color are added and the Polysorbate 20 and the propylene glycol are omitted. The resultant product is a clear green liquid shampoo with a viscosity of 134 seconds.

All of the aforedefined shampoo formulations were of useful viscosity, and possessed good foaming properties, anti-microbial activity, cleaning efficacy and conditioning properties. Hair shampooed with these compositions felt exceptionally clean, was easy to comb and manageable.

Variations in the above formulations may be made. For example, other amine oxides may be substituted for the dimethyl myristylamine oxide such as the dimethyl laurylamine oxide, dimethyl cetylamine oxide and the like. Similarly other betaines may be substituted for the cocobetaine such as cocoamidopropyl betaine, cocamidoethyl sulfobetaine and the like. Other anionic sulfonate or sulfate surfactants may be substituted for the triethanolammonium lauryl sulfate or the fatty alcohol-ethylene oxide sodium sulfate.

Likewise, the amounts of each of the anionic and amphoteric components as well as the ethanolamide, nonionic surfactant and alcohol may be varied within the designated percentages aforedefined without adversely affecting the solubility of the antidandruff agent.

The invention has been described with respect to various examples and embodiments but it is not to be limited to these because it is evident that one of skill in the art with the present application before him will be able to utilize substituted and equivalents without departing from the spirit of the invention.

We claim:

1. A clear, homogeneous, liquid, anionic-amphoteric based, antimicrobial, conditioning shampoo consisting essentially of 0.5% to 2.5% by weight of 1-imidazolyl-1-(4-chlorophenoxy)-3,3-dimethylbutan-2-one solubilized in about 65 to 80% of an aqueous vehicle containing 12% to 25% by weight of a water-soluble anionic, sulfated or sulfonated detergent containing an alkyl radical of 10 to 18 carbon atoms in its molecular structure, 0.5% to 5% by weight of a water-soluble amphoteric surfactant selected from the group consisting of a betaine, amidobetaine, sulfobetaine or amidosulfobetaine surfactant having an alkyl group of 10 to 16 carbon atoms in its molecular structure and 1% to 6% by weight of a $C_{10}$-$C_{18}$ fatty acid mono- or di-ethanolamide.

2. A shampoo in accordance with claim 1, wherein the aqueous vehicle contains in addition 1% to 5% about by weight of a nonionic surfactant selected from the group consisting of a polyoxyethylene hexitan mono $C_{10}$-$C_{20}$ fatty acid ester having 10-80 mols of ethylene oxide per mole, a dimethyl $C_{10}$-$C_{16}$ alkyl amine oxide, and mixtures thereof.

3. A shampoo in accordance with claim 2, wherein said nonionic surfactant is dimethyl myristylamine oxide.

4. A shampoo in accordance with claim 3, wherein the ethanolamide is lauric myristic diethanolamide.

5. A shampoo in accordance with claim 4, wherein the betaine is cocodimethyl betaine.

6. A shampoo in accordance with claim 1, wherein the aqueous vehicle contains in addition about 0.5-2% by weight of a $C_2$-$C_3$ aliphatic monohydric and/or polyhydric alcohol.

7. A shampoo in accordance with claim 1, wherein the anionic surfactant is triethanolammonium lauryl sulfate.

8. A shampoo in accordance with claim 2, which contains in addition 0.5-2% by weight of a $C_2$-$C_3$ monohydric or dihydric alcohol.

9. A method of preparing the clear, homogeneous, liquid, anionic-amphoteric based, antimicrobial, conditioning shampoo of claim 1 which comprises the sequential steps of first dissolving said imidazolyl compound in said fatty acid mono- or di-ethanolamide with agitation and subsequently adding thereto with agitation said amphoteric surfactant followed by said anionic detergent and water to form a clear, liquid shampoo.

* * * * *